US00PP36913P2

(12) United States Plant Patent
Valin

(10) Patent No.: US PP36,913 P2
(45) Date of Patent: Sep. 2, 2025

(54) ***WEIGELA* PLANT NAMED 'TMWG19-103'**

(50) Latin Name: *Weigela florida*
Varietal Denomination: TMWG19-103

(71) Applicant: Branded Garden Products Ltd., Ipswich (GB)

(72) Inventor: Charles Valin, Ipswich (GB)

(73) Assignee: Branded Garden Products LTD, Ipswich (GB)

( * ) Notice: Subject to any disclaimer, the term of this patent is extended or adjusted under 35 U.S.C. 154(b) by 0 days.

(21) Appl. No.: 19/197,653

(22) Filed: May 2, 2025

Related U.S. Application Data

(63) Continuation of application No. 18/186,175, filed on Mar. 19, 2023.

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — Weatherly IP Solutions, LLC; James M. Weatherly

(57) ABSTRACT

A new cultivar of *Weigela* plant named 'TMWG19-103' that is characterized by a compact mounded growth habit and bright orange-red foliage in early spring before the onset of flowers. Plants of 'TMWG19-103' bear dark red-purple flowers and buds in profusion.

2 Drawing Sheets

CROSS REFERENCE TO RELATED APPLICATION

The present application is a continuation of and claims priority to U.S. application Ser. No. 18/186,175, as filed on Mar. 19, 2023, the entire contents of which are incorporated herein by reference for all purposes.

Genus and species: *Weigela florida.*

Variety denomination: 'TMWG19-103'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'TMWG19-103'.

'TMWG19-103' originated from a *Weigela* breeding program which the inventor carried out at the inventor's nursery in Ipswich, United Kingdom. The inventor had assembled a collection of *Weigela* varieties (both commercial varieties and inventor's proprietary selections). After hand pollination between many of the assembled plants, seeds were collected, sown, grown on and planted in the field for evaluation. The identities of the parents of 'TMWG19-103' are unknown.

The new cultivar 'TMWG19-103' was selected in the field in 2018 for its combination of compact habit, bright orange-red foliage in early spring (prior to flowering), and deep red flowers borne profusely.

The inventor first asexually reproduced 'TMWG19-103' in 2018 by the method of softwood cuttings. The inventor has determined that the unique characteristics of 'TMWG19-103' are stable and reproduce true to type in successive generations of asexual reproduction.

SUMMARY

The following traits have been repeatedly observed and represent the characteristics of the new *Weigela* cultivar 'TMWG19-103'. 'TMWG19-103' has not been tested under all possible conditions and phenotypic differences may be observed with variations in environmental, climatic and cultural conditions, however, without any variance in genotype.

1. 'TMWG19-103' exhibits a compact mounded growth habit.
2. Mature fully flowering plants of 'TMWG19-103' achieve a height of 50 cm. to 55 cm. and a width of 65 cm. to 70 cm.
3. Plants of 'TMWG19-103' bear bright orange-red foliage in early spring, prior to flowering.
4. Plants of 'TMWG19-103' are extremely floriferous: a mature plant of 'TMWG19-103' may bear 45 flowering stems and approximately 600 flowers are open at one time.
5. Plants of 'TMWG19-103' are early to flower. A mature plant is in full flower in early April to mid-April in California.
6. The flowers and flower buds of 'TMWG19-103' are dark red-purple in color.
7. 'TMWG19-103' grows well in moist well-drained soils in full sun to partial shade.
8. 'TMWG19-103' is hardy at least to USDA Zone 5.

BRIEF DESCRIPTION OF THE PHOTOGRAPHS

Figure 1:
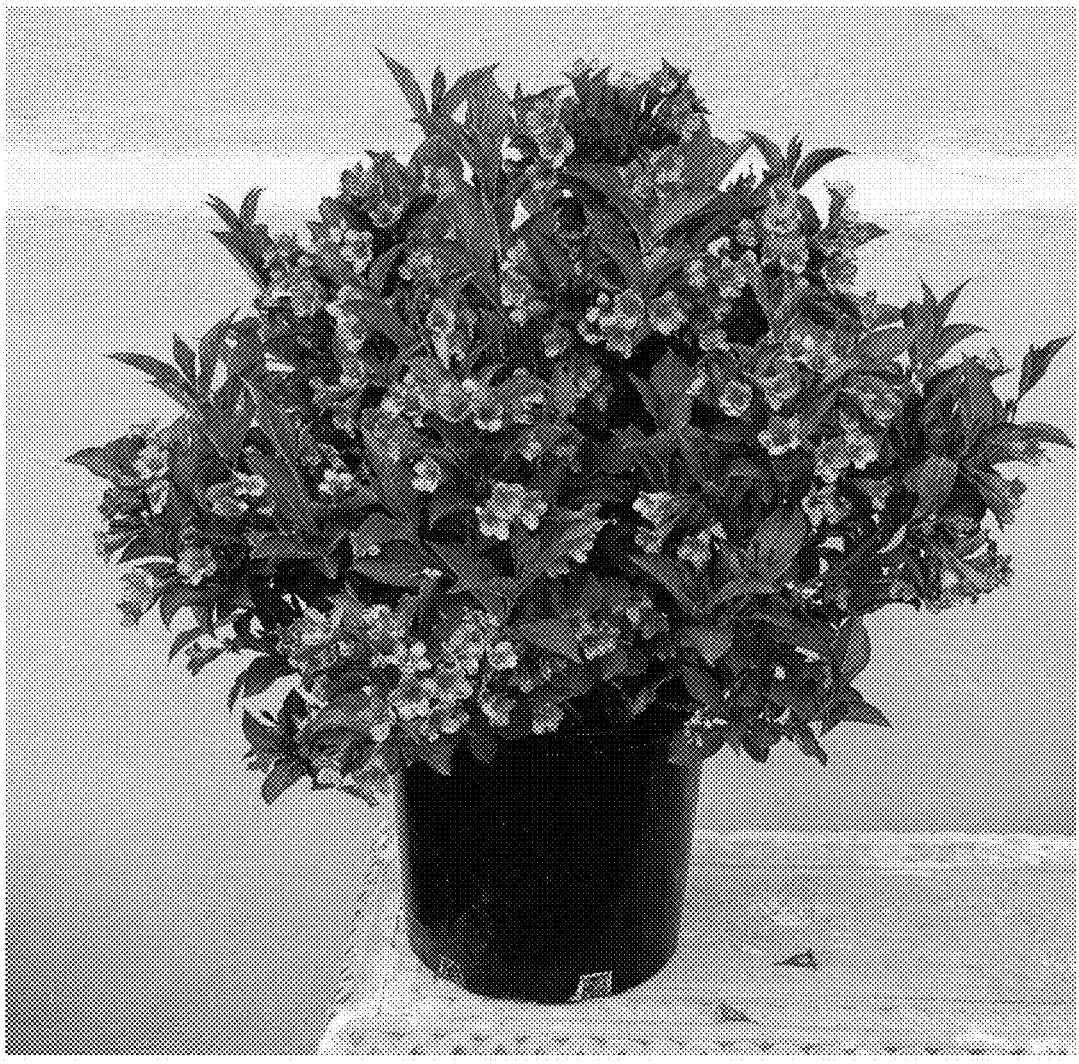
Figure 2:
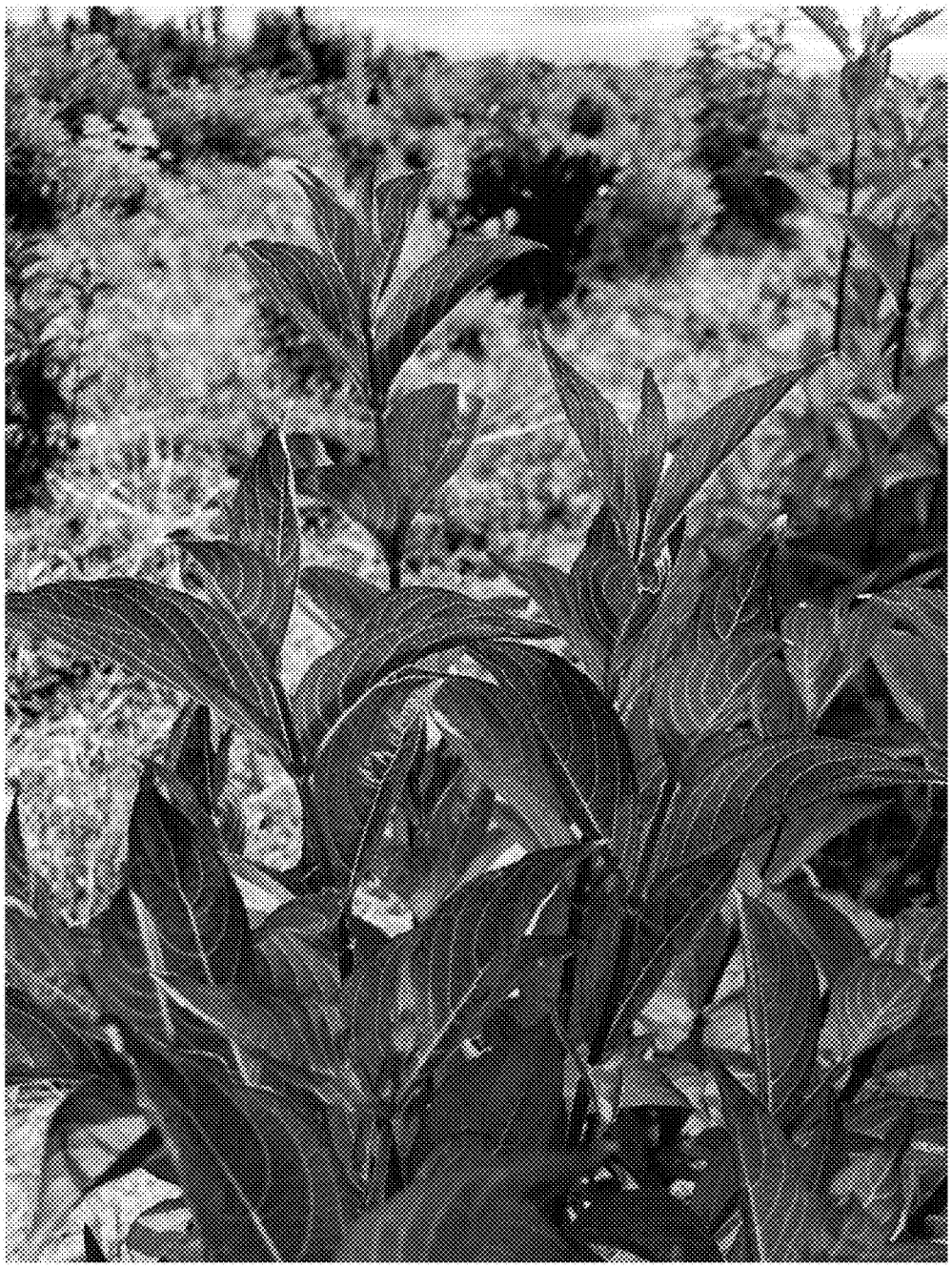

The accompanying color photographs in FIG. 1 and FIG. 2 illustrate the overall appearance of the new *Weigela* variety 'TMWG19-103' showing colors as true as it is reasonably possible to obtain in colored reproductions of this type. Colors in the photographs may differ from the color values cited in the detailed botanical description, which accurately describe the actual colors of the new variety 'TMWG19-103'. No chemicals were used to treat the illustrated plant.

FIG. 1 depicts a whole plant of 'TMWG19-103' in mid-April. The illustrated plant is four years old and is growing in a 3.7-gallon container. The plant has been grown entirely outdoors in Santa Barbara, California.

FIG. 2 depicts the orange-red new foliage growth of 'TMWG19-103'. The photograph in FIG. 2 was taken from the same plant as illustrated in FIG. 1 before the onset of flowering.

BOTANICAL DESCRIPTION OF THE PLANT

The following is a detailed description of the new cultivar 'TMWG19-103'. Data was collected in mid-April from fully flowering four-year old plants grown in 3.7 gallon (14 liter) containers in Santa Barbara, California. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Weigela*.

Botanical classification: *Weigela*.
- *Variety*.—'TMWG19-103'.
- *Species*.—*florida*.

Parentage:
- *Female parent*.—Unknown.
- *Male parent*.—Unknown.

Plant description:
- *Growth habit*.—Compact mound.
- *Use*.—In containers and in the landscape.
- *Suitable container sizes*.—1 gallon, 3 gallon and larger.
- *Dimensions*.—50 cm. to 55 cm. in height, and 65 cm. to 70 cm. in width.
- *Hardiness*.—At least hardy to USDA Zone 5.
- *Propagation*.—Stem cuttings.
- *Time to initiate roots*.—5 to 6 weeks are required to produce roots on an initial cutting.
- *Crop time*.—9-10 months to produce a first year flowering plant in a small container. Additional years to produce larger specimen plants.
- *Root system*.—Fibrous.
- *Light*.—Plant in full sun or partial shade.
- *Soil*.—Plant in moist but well drained soil.
- *Type*.—Deciduous shrub.
- *Seasonal interest*.—Extremely floriferous in early-mid spring.

Stem (below first pinch or stop):
- *Shape*.—Terete.
- *Dimensions*.—2 cm. in length, 1.5 cm. in diameter.
- *Color*.—197B.
- *Surface*.—Lignified, rough, glabrous.

Branches:
- *Quantity*.—Approximately 45 primary and lateral branches.
- *Branch stem dimensions*.—45 cm. to 55 cm. in length, 5 mm. to 8 mm. in diameter.
- *Shape*.—Terete.
- *Internode length*.—2.5 cm. to 5.5 cm.
- *Branch stem color* (*new growth*).—Ranges between 45A and 46A.
- *Branch stem color* (*previous years' growth*).—199D.
- *Surface* (*new growth*).—Glossy, puberulent, hairs very short and fine, less than 0.5 mm in length, color NN155D.
- *Surface* (*previous years' growth*).—Lignified, smooth, glabrous.
- *Lenticels* (*present on previous years' growth only*).—Spaced 3 mm. to 5 mm. apart, elliptic, length 2.5 mm., width 1.5 mm., raised approximately 0.5 mm., color 197A.

Foliage:
- *Leaf arrangement*.—Opposite.
- *Leaf division*.—Simple.
- *Leaf shape*.—Ovate, longitudinally inwardly curved.
- *Leaf attachment*.—Short petiolate.
- *Petiole shape*.—Sulcate, adaxial surface concave.
- *Petiole dimensions*.—4 mm. in length and 2 mm. in width.
- *Petiole color*.—145C.
- *Petiole margins*.—Pubescent, hairs very fine, length 0.5 mm., color NN155D.
- *Leaf dimensions* (*maximum*).—80 mm. in length, 40 mm. in width.
- *Leaf surface* (*both*).—Glabrous.
- *Leaf color* (*new spring growth, both surfaces*).—34A as leaf opens, becoming 34A and 146A as leaf expands.
- *Leaf color* (*mature leaves, adaxial surface*).—138A.
- *Leaf color* (*mature leaves, abaxial surface*).—138B, tinged 64A.
- *Leaf apex*.—Narrowly acute.
- *Leaf base*.—Cuneate.
- *Leaf margin*.—Finely serrate.
- *Leaf venation pattern*.—Pinnate.
- *Veins* (*new spring growth, adaxial surface*).—Midrib very slightly raised, vein color 144C to 144D.
- *Veins* (*new spring growth, abaxial surface*).—Midrib strongly raised 0.5 mm. to 1.0 mm., vein color ranges between 171C and 178C.
- *Veins* (*mature leaves, adaxial surface*).—Color 138A except flat midrib 145C.
- *Veins* (*mature leaves, abaxial surface*).—Color 138B except midrib 146D. Midrib raised 1 mm. towards leaf base.

Inflorescence, flowers:
- *Inflorescence form*.—Cymose.
- *Flowers arrangement*.—Flowers present at each node, in each opposite leaf axil.
- *Quantity of flowers per node*.—2 or 4 or 6 (1 or 2 or 3 per axil).
- *Quantity of flowers per plant*.—Approximately 600 flowers at peak flowering (2-6 flowers per node, 3-4 nodes per stem, 45 flowering stems).
- *Flower aspect*.—Outward and upward facing.
- *Diameter of fully developed flower* (*at flower tube apex*).—30 mm. as presented, 34 mm. measured when flattened.
- *Length of flower, including corolla tube*.—40 mm.
- *Bud*.—Shape: Truncated cone, wider at apex. Color: 59B. Dimensions: 30 mm. in length, 9 mm. in diameter at apex. Surface: Appears minutely glandular, semi-glossy.
- *Bracteoles*.—Arrangement: Where present, borne singly or in unequal pairs at the base of peduncle. Shape: Narrowly lanceolate. Dimensions: 1 mm. to 3 mm. in length, 1 mm. in width at base. Color: 180A to 180B. Surface: Glabrous.
- *Peduncle*.—Dimensions (buds): 14 mm. in length and 1 mm. in diameter. Dimensions (flowers): 15 mm.-20 mm. in length and 1 mm. in diameter. Shape: Round. Color: 59A (buds), 184A (flowers). Surface: Smooth, glossy.

*Calyx, sepals.*—Shape: Narrow funnel-shaped. Calyx diameter: 6 mm. measured across sepal apices. Sepals: 5 in number, fused towards and at base. Sepal dimensions: 8 mm. to 9 mm in length, 2 mm. in width. Sepal color (both surfaces): 179A at base, becoming darker 183A at apex. Sepal surface (both surfaces): Matte, puberulent.

*Corolla* (*tube and fused petals to base of free petal lobes*).—Shape: Salverform. Dimensions: 28 mm. to 30 mm. in length, 2 mm. in diameter at base, 13 mm. in diameter at base of petal lobes. Tube color (both surfaces): 63A. Tube surface: Glabrous. Petals (free petal lobes): Number: 5, fused at base. Petal lobe shape: Orbicular. Petal lobe color (both surfaces): 63B. Surface texture: Glabrous.

Reproductive organs:

*Number of stamens.*—5, individually fused to corolla tube at base.

*Dimensions* (*filaments*).—18 mm. in length, 7 mm. where fused, 11 mm. free; diameter 0.75 mm. to 1.0 mm. in diameter.

*Filament color.*—63A where fused, becoming 63B where free except N155A below anthers.

*Anther shape.*—Narrow elliptical, centrally dorsifixed.

*Anther dimensions.*—5 mm. in length and 0.75 mm.-1 mm. in width.

*Anther color.*—162D.

*Pollen amount.*—Sparse (none on some flowers).

*Pollen color.*—158B.

*Number of pistils.*—1.

*Style.*—Round, 39 mm. in length and 0.75 mm. in diameter.

*Style color.*—38A towards base, becoming NN155D centrally and N155B below stigma.

*Style surface.*—Glabrous.

*Stigma shape.*—Capitate (flattened sphere) or bi-lobed.

*Stigma dimensions.*—3 mm. in diameter or 3 mm. x 2 mm. (bi-lobed); 2 mm. in height.

*Stigma color.*—158B.

*Ovary.*—Observed immature only (absent on most flowers).—Superior, ovoid, 1.5 mm. in length and 1 mm. in diameter, color 152B, smooth, glossy.

Fruit: None observed.

Seed: None observed.

Susceptibility or resistance to pests and diseases: None.

COMPARISON WITH PARENT VARIETIES

The parents of 'TMWG19-103' are unknown. No comparison is available.

COMPARISON WITH CLOSEST KNOWN VARIETY

'TMWG19-103' may be compared with *Weigela* plant named 'Wings of Fire' (U.S. Plant Pat. No. 21,920). Whereas both varieties, 'TMWG19-103' and 'Wings of Fire' are similarly compact in habit, the plant form of 'TMWG19-103' is mounding and the plant habit of 'Wings of Fire' is upright. The two varieties differ by foliage color and flower color. The foliage color of 'TMWG19-103' is bright orange-red in the spring, with older foliage becoming light green during the summer months. The spring foliage color of 'Wings of Fire' is green with tinges of grey-orange, becoming mostly grey-orange in the summer months. The flowers of 'TMWG19-103' are slightly smaller than the flowers of 'Wings of Fire'. The flowers of 'TMWG19-103' are dark red-purple in color whereas the flowers of 'Wings of Fire' are paler pink-red in color.

I claim:

1. A new and distinct cultivar of *Weigela* plant named 'TMWG19-103' as described and illustrated herein.

* * * * *